United States Patent
Berlinger et al.

(10) Patent No.: US 9,014,424 B2
(45) Date of Patent: Apr. 21, 2015

(54) TRACKING REPRESENTATIONS OF INDICATOR BODY PARTS

(75) Inventors: Kajetan Berlinger, Münich (DE); Stephan Brumme, Potsdam (DE)

(73) Assignee: Brainlab AG, Feldkirchen (AG)

( * ) Notice: Subject to any disclaimer, the term of this patent is extended or adjusted under 35 U.S.C. 154(b) by 207 days.

(21) Appl. No.: 13/581,504

(22) PCT Filed: Mar. 2, 2010

(86) PCT No.: PCT/EP2010/052619
§ 371 (c)(1),
(2), (4) Date: Dec. 7, 2012

(87) PCT Pub. No.: WO2011/107145
PCT Pub. Date: Sep. 9, 2011

(65) Prior Publication Data
US 2013/0072745 A1    Mar. 21, 2013

(51) Int. Cl.
*G06K 9/00*    (2006.01)
*A61N 5/10*    (2006.01)
(Continued)

(52) U.S. Cl.
CPC .............. *A61N 5/1049* (2013.01); *G06T 7/004* (2013.01); *G06T 7/2026* (2013.01); *G06T 7/2046* (2013.01); *G06T 2207/10076* (2013.01); *G06T 2207/10081* (2013.01); *G06T 2207/10088* (2013.01); *G06T 2207/20021* (2013.01); *G06T 2207/30008* (2013.01); *G06T 2207/30096* (2013.01); *G06T 2207/30241* (2013.01);
(Continued)

(58) Field of Classification Search
None
See application file for complete search history.

(56) References Cited

U.S. PATENT DOCUMENTS

| | | | |
|---|---|---|---|
| 6,295,464 B1 * | 9/2001 | Metaxas | 600/407 |
| 6,778,689 B1 * | 8/2004 | Aksit et al. | 382/128 |
| 7,260,426 B2 * | 8/2007 | Schweikard et al. | 600/407 |

(Continued)

FOREIGN PATENT DOCUMENTS

EP    08 169 422.6    11/2008
EP    09 160 153.4    5/2009

OTHER PUBLICATIONS

U.S. Appl. No. 12/621,881, filed Nov. 2009, Berlinger et al.
(Continued)

*Primary Examiner* — Tsung-Yin Tsai
(74) *Attorney, Agent, or Firm* — Tucker Ellis LLP

(57) ABSTRACT

The present invention relates to a method for tracking image sections which represent indicator body parts of a body in a process sequence of images, wherein changes in the position of the indicator body parts are used as an indicator for changes in the position of a treatment body part of the body which is to be treated using a treatment beam, said method comprising the following steps: providing advance image data which describe an advance sequence of images representing a result of an advance analysis of the body; providing process image data which describe the process sequence of images, wherein the process sequence of images represents a result of a process analysis of the body which is performed after the advance analysis; determining, on the basis of the advance image data, sub-images which undergo similar changes in position in the advance sequence; extracting, on the basis of the process image data and the determined sub-images, image sections from the images of the process sequence which have an image content which corresponds to the image content of the determined sub-images; and tracking the extracted image sections in the process sequence.

14 Claims, 6 Drawing Sheets

(51) Int. Cl.
*G06T 7/00* (2006.01)
*G06T 7/20* (2006.01)

(52) U.S. Cl.
CPC . *A61N2005/1055* (2013.01); *A61N 2005/1061* (2013.01); *A61N 2005/1087* (2013.01)

(56) References Cited

U.S. PATENT DOCUMENTS

| 7,725,163 | B2* | 5/2010 | Schmitz et al. | 600/425 |
|---|---|---|---|---|
| 2003/0120145 | A1* | 6/2003 | Schmitz et al. | 600/407 |
| 2004/0092815 | A1* | 5/2004 | Schweikard et al. | 600/425 |
| 2005/0053196 | A1* | 3/2005 | Mostafavi | 378/98.12 |
| 2005/0053267 | A1* | 3/2005 | Mostafavi | 382/128 |
| 2005/0054916 | A1* | 3/2005 | Mostafavi | 600/427 |
| 2007/0291104 | A1* | 12/2007 | Petersen et al. | 348/14.01 |
| 2008/0144772 | A1* | 6/2008 | Yi et al. | 378/65 |
| 2009/0262894 | A1* | 10/2009 | Shukla et al. | 378/65 |
| 2010/0266099 | A1* | 10/2010 | Busch et al. | 378/65 |
| 2011/0007309 | A1* | 1/2011 | Stewart et al. | 356/301 |

OTHER PUBLICATIONS

U.S. Appl. No. 12/622,002, filed Nov. 2009, Berlinger et al.
Lhuillier et al., "Efficient Dense Matching for Textured Scenes Using Region Growing", Proceedings of the British Machine Vision Conference, XX, XX No. 2, Jan. 1998, pp. 700-709.
Lin et al., "Tumor Targeting for Lung Cancer Radiotherapy Using Machine Learning Techniques", Machine Learning and Applications 2008 ICMLA '08 Seventh International Conference on IEEE, Dec. 2008, pp. 533-538.
Schweikard et al., "Fiducial-Less Respiration Tracking in Radiosurgery", Lecture Notes in Computer Science, vol. 3217, Jan. 2004, pp. 992-999.
International Search Report for International Application No. PCT/EP2010/052619 dated May 3, 2010.

* cited by examiner

TRACKING REPRESENTATIONS OF INDICATOR BODY PARTS

This application is a national phase of International Application No. PCT/EP2010/052619 filed Mar. 2, 2010 and published in the English language.

The present invention relates to the technical field of tracking representations of indicator body parts. Indicator body parts are body parts which are used as an indicator for changes in the position of another body part which is to be treated using treatment radiation, in particular ionising radiation. The body parts to be treated are referred to in the following as "treatment body parts". The body parts used as the above-described indicator are referred to in the following as "indicator body parts".

Reference is made to the patent applications EP 08 169 422.6 and EP 09 160 153.4 and the corresponding US patent applications U.S. Ser. No. 12/621,881 and U.S. Ser. No. 12/622,002. The disclosure of these applications is hereby incorporated by reference.

The present invention relates to the field of medicine and in particular to the use of radiation in order to treat parts of the body. Ionising radiation is in particular used for this purpose which in particular comprises or consists of particles (for example, subatomic particles or ions) or electromagnetic waves which are energetic enough to detach electrons from atoms or molecules and so ionise them. The treatment radiation is in particular used in radiation therapy or radiotherapy, in particular in the field of oncology. For the treatment of cancer in particular, the parts of the body comprising the tumour (the treatment body parts) are treated using the ionising radiation. Since the body and in particular the treatment body parts move during the radiation treatment, it is advantageous to control the position of the treatment beam such that the treatment beam hits the treatment body parts as accurately as possible.

The movements of the treatment body parts are in particular due to movements which are referred to in the following as "vital movements". Reference is also made in this respect to the above-mentioned applications EP 08 169 422.6 and EP 09 160 153.4, which discuss these vital movements in detail. In order to determine the position of the treatment body parts, analytical devices such as x-ray devices, CT devices or MRT devices are used to generate analytical images (such as x-ray images or MRT images) of the body. Analytical devices are in particular devices for analysing a body of a patient, for instance by using waves and/or radiation and/or beams of energy, in particular electromagnetic waves and/or radiation, ultrasound waves, particles beams. Analytical devices are in particular devices which generate images (for instance two- or three-dimensional images) of the body of the patient (in particular of internal structures and/or anatomical parts) by analysing the boy. Analytical devices are in particular used in medical diagnosis, in particular in radiology. However, it can be difficult to identify the treatment body part within the analytical image. It can in particular be easier to identify an indicator body part which correlates with changes in the position of the treatment body part and in particular the movement of the treatment body part. Thus, tracking an indicator body part allows a movement of the treatment body part to be tracked on the basis of a known correlation between the changes in the position (in particular the movements) of the indicator body part and the treatment body part.

It is an object of the present invention to reliably track an indicator body part.

This object is solved by the subject-matter of the independent claims. The dependent claims are directed to advantageous embodiments.

The inventor of the present invention has recognised that a sequence of analytical images of a body show different kinds of movement by the body parts represented in the analytical images of the sequence. The body parts represented by the analytical images are subject to vital movements (see for instance EP 08 169 422.6 and EP 09 160 153.4 as mentioned above). This means that the body parts are moved due to vital functions of the body such as respiration and/or the beat of the heart. Different body parts undergo different changes in position depending on the cause of the vital movement. The magnitude, direction, velocity, acceleration and/or frequency of a change in position can for example differ in accordance with the cause of the change in position and/or in accordance with the position or type of the body part which undergoes the change in position. Body parts moved by the beat of the heart, for example, generally show a smaller amplitude in their changes in position than body parts which are moved due to respiration. In particular, the direction of changes in position, in particular the direction of movements, can differ depending on the cause, i.e. for example, the direction of a movement by a body part caused by respiration differs from the direction of a movement by a body part caused by the beat of the heart. The frequency of changes in position is also for example higher if they are caused by the beat of the heart than if they are caused by respiration.

If, for example, bone structures such as ribs and a diaphragm are shown in an analytical image, these body parts can undergo different changes in position, in particular in different directions, even if due to the same cause such as for instance respiration. The differences between the changes in position are then in particular due to the different types of body parts and/or due to the different positions of the body parts. It is possible for the treatment body part (for example, the tumour) to undergo changes in position which differ from both the changes in the position of the diaphragm and the changes in the position of the bone structure (ribs). The present invention advantageously uses a sequence of analytical images to track the change in the position of indicator body parts in a manner which allows the changes in the position of the indicator body parts to be correlated with the changes in the position of a treatment body part, even if the body parts undergo different changes in position.

Advantageously, different changes in the position of different indicator body parts are identified in accordance with the invention. Tracking the indicator body parts on the basis of this identification is then more reliable, i.e. more robust. In accordance with the invention, parts of the sequence of analytical images are extracted or in other words filtered from the images. These extracted parts of the images are referred to in the following as "sections". The sections are preferably extracted (filtered) such that the extracted sections represent indicator body parts which (are likely to) undergo similar changes in position (i.e. in particular similar to each other and/or to predefined changes in position). In particular, the movement of the (image content included in the) sections is similar from image to image within the sequence. In the following, this characteristic will be referred to more concisely by stating that the movements of the sections are similar. If sections which show similar movements are tracked, then such tracking is more robust against any disruptive or interfering effects from other sections which undergo different movements. Moreover, if sections showing similar changes in position are extracted, then these sections will all show a similar correlation with the changes in the position of the treatment body part. This ultimately allows the position of the treatment body part to be determined more reliably on the basis of tracking the indicator body part. In order to correctly extract the sections for tracking the indicator body parts, in particular during the treatment (for example, a radiotherapy treatment), analytical images are preferably generated in advance, in particular before the treatment. The sequence of these analytical images is referred to in the following as the "advance sequence of images". The sequence of images used for tracking the indicator body parts, in particular during the treatment, is referred to as the "process sequence of images". The sections of images of the process sequence are preferably extracted (in particular determined and/or selected) on the basis of knowledge gathered by analysing the advance sequence. In particular, the advance sequence is analysed for any similarity in the changes in the position of sub-images in the advance sequence. Based on this analysis, the location (and/or geometry) of the sections to be extracted can be determined, for instance by assuming that the sections will have relative positions (and/or geometries) in the process sequence which correspond to or are at least similar to the positions (and/or geometries) of the sub-images relative to each other in the advance sequence, wherein said sub-images are determined to be sub-images which undergo similar changes in position, and in particular by assuming that the image sections have the same or a similar image content to the sub-images. A set of image sections can thus be identified within an image of the process sequence, on the basis of a set of sub-images which have been determined to be sub-images which undergo similar changes in position. Thus, it is highly likely that the image sections of the identified set of image sections will also undergo similar changes in position in the process sequence, which enables the indicator body parts to be tracked more robustly. Thus, the set of image sections and the set of sub-images preferably show the same indicator body parts.

In particular, the set of image sections is determined on the basis of the (assigned) set of sub-images such that its image content corresponds (as exactly as possible) to the image content of the latter. Image recognition methods such as pattern recognition methods can be used for this purpose. In particular, the geometry (size and/or shape) of the sub-images of the set of sub-images is the same as the geometry (size and/or shape) of the image sections of the set of image sections. A search is in particular performed by means of the image recognition method in an image of the process sequence for a set of image sections (the image content of) which is as similar as possible to the (image content of the) set of sub-images (of one of the images of the advance sequence). If there are several similar sets of image sections, the one exhibiting the greatest similarity is selected. A measure of the similarity can for example be the sum of the magnitudes or the squares of the magnitudes of the difference between the pixel values of a difference pattern, where the difference pattern is formed from a candidate for a set of image sections and the set of sub-images. It is also possible to determine a correlation coefficient, which describes the correlation between the set of sub-images and the set of image sections, as a measure of their similarity. In particular, a set of image sections "corresponds" to a set of sub-images if it has at least a predetermined degree of similarity with respect to the image content, in particular if the degree of similarity of the set of image sections exhibits the maximum similarity when compared with other sets of image sections. The same definition applies to the correspondence between a sub-image and an image section. Where magnitudes or squares of magnitudes are determined, the maximum similarity prevails if for example the magnitudes or squares of magnitudes are at a minimum. Where correlation coefficients are determined, the maximum similarity prevails for example if the correlation coefficients are at a maximum. In accordance with another embodiment, the image sections of a set of image sections in which the degree of similarity exceeds a threshold value and is thus sufficient represent candidates for a set of image sections. It is then possible to select a set of image sections from the candidates in accordance with other criteria such as are for instance explained in EP 08 169 422.6 with respect to selecting regions.

In accordance with one embodiment, a search mask is established which would only extract (let pass) the set of sub-images if applied to the image of the advance sequence which includes the set of sub-images and if applied at a particular position relative to the frame of this image. The search mask is then for example laid over the image of the process sequence in order to scan it (by displacing the search mask relative to the image), in order to identify the corresponding set of image sections. The image part which the search mask lets pass is compared with the set of sub-images. If, for example, the degree of similarity between the image part and the image content of the set of sub-images is sufficient, then the set of image sections has been identified. During the search procedure, the search mask is for instance displaced pixel by pixel relative to the image in steps, and the degree of similarity is determined at each step (and for instance compared with a predetermined threshold value). The search procedure is preferably continued until the entire image of the process sequence has been scanned using the search frame. The set of image sections which has the greatest similarity is then preferably selected. It goes without saying that the search method can also be optimised to make it faster, such that in a favourable case, the search is not performed pixel by pixel but in a more targeted way.

The term "geometry" covers size and/or shape. In particular on the basis of the analysis, the sections which undergo similar changes in position are selected. Where (a set, in particular group, of) body parts, image sections or sub-images are said to undergo (or perform) "similar changes in position", this means in particular that the (set, in particular group, of) body parts, image sections or sub-images undergo (or perform) changes in position which are similar to each other and/or similar to predefined changes in position.

The present invention relates in particular to a method for tracking the representations of indicator body parts. The representations are shown in the process sequence of images which are analytical images. The representations are tracked in the process sequence of images, in particular from one image of the process sequence to the next image of the process sequence. In order to perform this tracking, several steps are preferably performed, as described in the following.

In accordance with one step, first image data referred to as advance image data are provided. The advance image data describe a first sequence of images which is referred to as the advance sequence of images. The advance sequence results from an analysis of the body by an analytical device such as those mentioned above, for example an x-ray device or CT. This analysis is performed before tracking is performed and is accordingly referred to as the advance analysis.

Where data, regions or images are "provided", this means that they are ready for use by the method in accordance with the invention. The data, regions or images can achieve this state of being "provided" by for example being detected or captured (for example by an analytical device) or by being inputted (for example via interfaces). The data can also achieve this state by being stored in a memory (for example a ROM, CD and/or hard drive) and thus ready for use within the framework of the method in accordance with the invention.

Second image data, referred to as process image data, are preferably also provided. The process image data describe a second sequence of images which is referred to as the process sequence of images. These images are likewise analytical images. Preferably, the images of the process sequence and the images of the advance sequence are generated using the same device and/or in particular using the same generating conditions, such that an identical region of the body is shown in the images of the advance sequence and the images of the process sequence if the body does not move. In particular, the imaging geometry for acquiring the advance sequence and the process sequence is the same. The process sequence of images results from a so-called process analysis (second analysis) of the body which is performed after the advance analysis (first analysis), wherein the advance analysis of the body resulted in the advance sequence of images.

The provided data of at least parts of the patient's body can for example be obtained using medical imaging methods and by means of the analytical devices. This is understood to mean radiology methods, advantageously apparatus-based radiology methods, such as for instance computed tomography (CT), x-ray tomography, magnetic resonance tomography (MRT or MRI), conventional x-ray, sonography and/or ultrasound examinations, and positron emission tomography.

The advance analysis is in particular performed before the body is treated with the treatment radiation. The process analysis is preferably performed while the body is treated with the treatment radiation. The images acquired during the process analysis are preferably used immediately or at least without significant delay (preferably, for example, less than 1 second) in order to control the treatment radiation beam, in particular in order to steer said beam so that it hits the moving treatment body part.

The advance image data are preferably used to determine a similarity of the changes in the position of sub-images within the advance sequence of images. Sub-images are parts of the images of the advance sequence. There can be identical or at least similar sub-images in different images of the advance sequence at different positions (relative to the frame of the respective image). These sub-images are referred to as corresponding sub-images. There can be a sequence of corresponding sub-images in the advance sequence which describes a sequence of positions of corresponding sub-images (relative to the frames of the images). It can thus be said, in more intuitive terms, that a sub-image which represents the corresponding sub-images of the sequence undergoes changes in position from image to image in the advance sequence. Thus, there is a sequence of sub-images in the course of which a sub-image can have different positions in different images of the advance sequence. A sub-image therefore also has an average position relative to other sub-images in the sequence. The relative positions of the image sections (mentioned below) which are assigned to the sub-images undergoing changes in position can for instance correspond to the relative positions of the sub-images in one of the images of the advance sequence or to their average relative position. The corresponding sub-images in the sequence can be identified by searching for a sub-image which is as similar as possible to the previous sub-image in the sequence of sub-images. This can be performed in the same way as described above with respect to determining a set of corresponding image sections, i.e. a measure for determining the similarity between sub-images can for example be the sum of the magnitudes or squares of the magnitudes of the differences between the pixel values of the pixels which constitute the sub-images. A sub-image which results from such a search is an example of a sub-image which "corresponds" to the previous sub-image, on the basis of which the search was performed. If there are a plurality of sub-images (in an image of the above sequence) which are candidates for a sub-image which corresponds to a sub-image in a previous image of the advance sequence, then the candidate which has the greatest similarity, as indicated by the measure of similarity, is preferably selected.

The position of a sub-image can for example be defined with respect to the boundary (frame) of the image or with respect to the centre of the image. Thus, as mentioned above, the sub-image can "move" from image to image within the advance sequence (relative to the frames of the images), thereby undergoing "changes in position". If there are several different sub-images in one image of the advance sequence, then the changes in position which different sub-images undergo can be different or can be similar. Preferably, a determination is made in accordance with the invention as to whether the changes in the position of the sub-images are similar or not (or different or not), in particular for a plurality of sub-images. On the basis of this determination, it is in particular possible to know which sub-images undergo similar changes in position and which do not.

On the basis of the above-mentioned determination, it is then possible to extract image sections from the images of the process sequence which exhibit similar changes in position. This is in particular possible on the basis of the known relative positions of the sub-images in at least one of the images of the advance sequence or on the basis of the average relative positions. On the basis of this information on the relative positions of the sub-images which undergo similar changes in position, it is possible to determine the relative positions of the image sections within the images of the process sequence. The size and/or shape of the image sections correspond in particular to the size and/or shape of the sub-images which undergo similar changes in position. In particular, one of the image sections of the images of the process sequence is assigned to one of the sub-images of the images of the advance sequence. Preferably, each image section is respectively assigned to one of the sub-images of one of the images of the advance sequence. Preferably, the relative position and/or geometry (size and/or shape) of an image section is identical or at least similar (at least to a certain extent, for instance 80% or 90%) to the relative position and/or geometry of the assigned sub-image. The extracted image sections preferably fulfil the condition that the assigned sub-images have been determined to be sub-images which undergo similar changes in position, and in particular the condition that the image content of the set of image sections corresponds to the image content of the sub-images.

As mentioned above, the relative position and/or geometry (size and/or shape) of the sections to be extracted are preferably determined on the basis of the (assigned) sub-images which have been determined to be sub-images which undergo similar changes in position. This is in particular possible because it is assumed that the images of the advance sequence show the same region of the body as the images of the process sequence if the body does not move. The aforementioned method of extracting image sections thus allows the sections of the images of the process sequence which undergo similar changes in position to be filtered out. Advantageously, this in particular allows interfering influences from parts of the images in the process sequence which undergo different changes in position, and which are not extracted in accordance with the invention, to be reduced. These interfering influences would in particular occur when tracking the movements of indicator body parts.

As mentioned above, the relative positions of the image sections (relative to each other) which are extracted are preferably determined on the basis of the relative positions of the sub-images (relative to each other) in the images of the advance sequence, such that the sections respectively assume relative positions in the images of the process sequence at the same (or similar) relative positions as the relative positions which the sub-images respectively assume in at least one of the images of the advance sequence. The term "similar" means in particular a deviation in the relative positions, in particular a deviation in the distance and/or angle of direction, which is smaller than ten percent, five percent or one percent.

In accordance with the invention, tracking representations of the indicator body parts in the images of the process sequence is preferably based on the image sections which are extracted as mentioned above. This does not of course exclude the possibility of extracting different groups of image sections, wherein the changes in position (which the members of the groups undergo) are different from group to group but similar within each group. This extraction of image sections in groups will be explained in more detail below.

The representation of the indicator body parts can be tracked in different ways. The image content of the extracted individual image sections or the set of image sections is in particular analysed for changes in position from image to image within the process sequence. Due to the extraction, it may be assumed that at least the majority of the image content of the set of extracted image sections performs a similar movement from image to image within the process sequence. The image content of the set of extracted image sections includes representations of the indicator body parts.

As mentioned above, the image sections are preferably extracted such that the extracted image sections have a relative positional relationship to each other (positions relative to each other) which corresponds to the relative positional relationship (relative positions) between the sub-images which undergo similar changes in position. In particular, the size and/or shape of the sections also corresponds to the sub-images, as mentioned above. Accordingly, and as will be discussed below, a mask is preferably determined on the basis of the size and/or shape and/or relative positions of the sub-images, in order to extract a set of image sections. Preferably, a particular movement and/or trajectory of the representations of the indicator body parts is tracked on the basis of the set of extracted image sections (which are based on similar sub-images) only. For this purpose, changes in the position of the image content of the set of extracted image sections are preferably determined by comparing the image content of the set of extracted image sections of one image of the process sequence with the image content of the set of extracted image sections of another image of the process sequence. In other words, only the extracted part of the image which corresponds to the set of extracted image sections of the images of the process sequence is used as a basis for (usual) image tracking procedures. In particular, only the extracted part of a region is used for tracking, in the same way as is described in EP 08 169 422.6 with respect to tracking a region. The corresponding tracking procedure described in EP 08 169 422.6 (which corresponds to U.S. Ser. No. 12/621,881) is hereby incorporated by reference and will be discussed again below.

In accordance with one embodiment, the relative positions and/or shape and/or size of the extracted image sections are identical for all the images of the process sequence, as mentioned above. In accordance with another embodiment, the relative positions and/or sizes and/or shapes of the sections can change from image to image within the process sequence, in particular on the basis of an analysis of the advance sequence and/or on the basis of other parameters such as vital parameters, as will be explained in more detail below.

In accordance with a preferred embodiment, a region of an image is selected and a mask is applied to this region, as mentioned above. The masked region is then tracked in the process sequence in order to track changes in the position of the indicator body parts which undergo similar changes in position. Thus, in accordance with this preferred embodiment, the relative positional relationship (i.e. the relative positions) between the extracted sections are kept constant (fixed) during the tracking process by using a mask. Furthermore, the extracted sections are not tracked individually but rather as a group which is defined by masking the region. The region can change its position from image to image within the process sequence, as described in more detail in EP 08 169 422.6. Thus, in accordance with this embodiment, the change in the position of the set of extracted image sections (from image to image) is represented by the change in the position of the masked region from image to image within the advance sequence.

In accordance with another embodiment, the extracted sections are tracked individually, i.e. for example, sections are only extracted from one of the images, for instance the first image. Each of the sections is then tracked from image to image, in particular by searching for similar sections in the subsequent images of the process sequence (as explained above). The similarity of the image content of the sections is thus determined individually for each section. By contrast, in accordance with the aforementioned preferred embodiment which uses masked regions, the overall image content of the masked region of one image is preferably compared with the overall image content of a masked region of another region of the sequence. An optimiser can be used to identify the masked region of another image (in particular, the next image) in the sequence which is determined to be the masked region which corresponds to the masked region of the previous image. Alternatively, it is of course also possible to determine all the possible masked regions for each image and to compare them with the masked region of the previous image. The one which exhibits the greatest similarity to the masked region of the previous image (or one of the previous images) is then selected.

If the sections are tracked individually, it is possible for the sections to change their position relative to each other from image to image within the process sequence. Therefore, an average (for example, mean or median) change in the position of the sections from image to image is preferably determined. This average change in position is then determined to be the change in the position of indicator body parts which undergo similar changes in position. When searching for the individual sections in another image (in particular, the next image) of the process sequence, the relative positional relationship between the extracted sections is preferably used by a search algorithm to identify the sections which respectively correspond to the extracted sections of the previous image. Thus, the relative positions between the sections are not then fixed but rather flexible.

In accordance with another embodiment, which represents a sort of compromise between individually tracking sections and tracking a masked region, a search algorithm is applied which uses a flexible, for example not strictly fixed, positional relationship between the sections. Relative changes in position between the sections which are less than 10% or 5% or 1% are for example allowed. A mask can in particular be used in order to mask a region, the elements of which are allowed to undergo changes in position relative to each other within a predefined range and/or flexibly (in particular, elastically). Again, the change in the position of the region which is masked by the flexible mask is then preferably used to determine the changes in the position of the indicator body parts.

Mathematical expressions, in particular (physical) values or functions, are preferably determined in order to describe the changes in the position of the sub-images, in particular using physical quantities. The mathematical expressions which describe the changes in position are in particular physical quantities which represent these changes in position or result from them and which in particular quantify these changes in position and/or are functions of these changes in position (which are for example mathematically described or quantified). An example of the aforementioned mathematical expressions (for example, physical values) is for instance a vector which describes a change in the position of a sub-image in the advance sequence, for instance from a position of the sub-image in one of the images of the advance sequence to the position of the corresponding sub-image in another image of the advance sequence. The mathematical expression (for example, a physical value) can in particular be a function of the aforementioned vector, wherein the function can also be a function of identity, i.e. the function of the vector can for example be the vector itself. The mathematical expression can also be the function of a value. The value can also for example be the magnitude of the change in position, i.e. a distance. The function of the vector can be the direction of the change in position. Another example of the aforementioned mathematical expression (value) is a trajectory which describes a path of a sub-image in the advance sequence, in particular a path which the sub-image travels from image to image within the advance sequence. Another example of the aforementioned mathematical expression (for example, a physical quantity) is a time or a frequency at which a sub-image undergoes a cyclic (periodic) trajectory in the advance sequence. Such a frequency can in particular correspond to the frequency of respiration or to the frequency of the beat of the heart. The aforementioned time or frequency follows from the changes in the position of the sub-images.

In order to determine the similarity of the changes in the position of the sub-images, the aforementioned mathematical expressions (for example values or functions) determined for different sub-images are preferably compared with one another or with a mathematical expression (for example values or functions) which describe predetermined changes in position, for instance a frequency of respiration or a predetermined direction of changes in position. This direction is for example compared with the mathematical expression which describes the directions of changes in the position of the sub-images. If a similarity condition is fulfilled, i.e. if for example the direction of changes in the position of a sub-image is within a predetermined fixed angle of the predetermined direction, then the sub-image is determined to undergo similar changes in position, i.e. changes in position which are similar to the predetermined changes in position. Alternatively, the changes in position described by the mathematical expressions of the sub-images can be compared with each other. The sub-images which undergo changes in position which fulfil a similarity condition, for instance which are within a predetermined and predefined range (if for instance the compared directions only deviate within the above-mentioned fixed angle), will then be determined as sub-images which undergo similar changes in position, i.e. changes in position which are similar to each other.

As mentioned above, similarity conditions such as for instance predetermined ranges or upper or lower limits for the mathematical expressions are provided in order to assess whether there is similarity or not. These can for instance include a predetermined range for a frequency of respiration, a predetermined range for the direction of a change in position or a predetermined range for a magnitude of a change in position from image to image or a maximum limit for the percentage difference between changes in position.

Thus, the mathematical expression in the above-mentioned ranges can be used to establish conditions for deciding whether changes in position are similar or not. Different sub-images can fulfil different similarity conditions. For instance, one group of sub-images performs a high-frequency movement in accordance with the beat of the heart, while another group of sub-images performs a low-frequency movement which can for instance be explained by the frequency of respiration. Another group of sub-images can move in a first direction which can be a predetermined direction which has been predefined on the basis of the expected direction of movement of the diaphragm. Another group of sub-images can be similar to another predetermined direction which can be predefined on the basis of a predetermined assumed movement of the chest. Thus, the sub-images can be grouped in accordance with the similarity conditions which the changes in the position of the sub-images meet. All the members of a group, i.e. all the sub-images of a group, meet the same similarity condition. In particular, mathematical expressions are determined for the changes in the position of the sub-images. The changes in the position of the sub-images are in particular analysed by determining mathematical expressions for these changes in position. In particular, the same type of mathematical expression is determined for the sub-images, wherein said type can for instance be a value (for example a direction and/or magnitude of a change in position), a function describing the change in position, a trajectory describing a path of changes in position, and/or a time or frequency of the changes in position. The changes in position described by one type of mathematical expression are then compared with each other or with predetermined changes in position which are described by said type of mathematical expression. The changes in position which are described by said type of mathematical expression are determined to be similar or not on the basis of the similarity conditions. This can be repeated for other types of mathematical expression. Therefore, there may be one group which includes sub-images which undergo changes in position in similar directions and there may be another group which describes sub-images which undergo changes in position at a similar frequency. Again, the term "similar" can mean that the mathematical expressions (for example a direction or frequency) are similar to each other within a group and/or similar to a mathematical expression which describes predetermined changes in position.

In other words, groups of sub-images are identified on the basis of their determined similarity. All the members of a group undergo similar changes in position. In particular, all the members of a group undergo changes in position which are similar with respect to a particular type of mathematical expression.

Preferably, the method is provided with body position data. The body position data describe the position of the body or at least the part of the body which is to be treated using radiation and analysed by the analytical devices, relative to the analytical devices. Preferably, the body position data describe the relative position between the body (or part of the body) and the imaging geometry of the analytical devices. The imaging geometry is in particular defined by the path and/or direction of the radiation used for generating the image and/or by the location of the radiation source and/or the location of the image plane.

Preferably, predetermined condition data are also provided which describe predetermined similarity conditions in accordance with the position of the body (or body part) relative to the imaging geometry. In a reference table, for example, different relative body positions can be assigned to different similarity conditions. There can for example be several predefined similarity conditions for a particular relative body position described by the body position data. For instance, a first such similarity condition defines predetermined positional changes, for instance a predefined direction of movement from the inferior to the superior and vice versa which results from the movement of the diaphragm due to respiration and can be observed by the analytical device if the body is in the relative position described by the body position data. Another predefined similarity condition can be an anti-cyclic movement such as for instance a movement which is anti-cyclic with respect to the aforementioned inferior/superior movement and which is due to a movement of the chest and which can be observed by the analytical device if the body is in the same relative position described by the body position data. Another predefined condition can be a movement in the anterior/posterior direction (and vice versa) which is due to the movement of the chest and can be observed by the analytical device if the body is in the same relative position described by the body position data. Another predefined condition can for example be the heart rate or the like. For different positions, different conditions (which in particular define different directions) can be assigned to the different positions. In particular, the predefined directions change if the relative position of the body changes.

Preferably, vital data are provided in addition to or as an alternative to the body position data. Said vital data describe at least one vital parameter of the body, in particular at the time the images of the advance sequence are acquired. The vital data describe for example the patient's frequency of respiration during the acquisition of the advance sequence of images. The similarity condition is then a predetermined condition which is determined on the basis of the frequency of respiration, i.e. the sub-images which have a frequency of a cyclic movement which is similar to the frequency of respiration as described by the vital data are deemed to undergo similar changes in position. Thus, the similarity conditions are defined in accordance with the vital data.

Mathematical expressions, in particular physical quantities which are used to describe the changes in position or which result from changes in position, are described by at least one of the following: the direction of a change in position; the magnitude of a change in position; a trajectory; the frequency of periodic changes in position; a phase shift relative to a periodic change in position; the time of a periodic change in position.

In accordance with the method of the invention, the image content (represented by the extracted sections) or preferably at least the majority of the image content represents indicator body parts which undergo similar changes in position (movements) from image to image within the process sequence, as mentioned above. However, it is possible during these movements for some of the indicator body parts (which undergo similar changes in position) to leave certain image sections without subsequently emerging in other image sections, such that the corresponding image content is not available for tracking. On the other hand, it is possible for new image content to enter the image sections which represents indicator body parts which undergo dissimilar changes in position, i.e. changes in position which are not similar to at least the majority of the image content of the image sections. In order to flexibly adapt to such changes in the image content of the image sections, it is in accordance with another embodiment if the relative positions of the image sections (relative to each other) and the size and/or shape of the image sections are not fixed, i.e. can change from image to image within the process sequence. If the relative positions of the sub-images are for example fixed, the average relative positions (for example, mean positions) of the sub-images in the images of the advance sequence are used to define corresponding relative positions of the image section in the images of the process sequence, while in accordance with another embodiment, the relative position of the image sections can change. Thus, the absolute change in the position of an image section from image to image within a process sequence can be different for different image sections. As mentioned above, the set of image sections corresponds to a set of sub-images. The advance sequence provides information about the change in relative position between the sub-images of the set during the acquisition of the advance sequence of images. The change in relative position between the sub-images can for example be linked to vital parameters which are measured during the acquisition of the advance sequence of images and described by the advance vital data. Vital parameters are preferably also measured during the acquisition of the process sequence and described by process vital data. A correlation between the changes in the position of the sub-images relative to each other and the advance vital data can then be determined. This correlation can be used to determine changes in the relative positions of the image sections of the set of image sections which corresponds to the set of sub-images, on the basis of the process vital data. If the sub-images are grouped as mentioned above, the correlation is preferably determined group for group, i.e. separately for each group. Preferably, only one vital parameter is ultimately selected from each group for determining the correlation. Where the correlation is determined for different vital parameters for one group, the correlation which exhibits the strongest correlation is of course preferably selected.

As mentioned above, process vital data are preferably provided which describe at least one vital parameter of the body for the images of the process sequence, in particular for the current process image. Assuming the same correlation exists between the vital parameter described by the process vital data and the relative changes in the position of the image sections relative to each other and/or their change in geometry as exists between the same vital parameter and the changes in the position of the sub-images (of one of the groups) relative to each other and/or their change of geometry, then the determined (and selected) correlation is used to determine the change in relative position of the image sections in the images of the process sequence, in particular in the current process image. Thus, the relative positions and/or the geometry of the image sections can be flexibly determined using the determined correlation and the process vital data for each of the images of the process sequence. In this way, determining the image sections can in particular be adapted to the change in image content due to different movements of the body parts in different layers of the body. For instance, a body part emerges below a bone structure from image to image in the process sequence in accordance with the amplitude of respiration as described by the advance vital data and process vital data.

The geometry (the shape and/or size) of the sub-images and image sections can be equal. In particular, the images of the advance sequence can be tessellated. Each element of the tessellation is then a sub-image. Accordingly, the images of the process sequence or a region of them can be tessellated, and each element resulting from the tessellation is an image section. The images of the advance sequence or a region of them can be tessellated in the same way as the images of the process sequence or a region of them. Thus, each sub-image is assigned one image section of the same size. It is of course also possible to tessellate in other ways, for example such that several image sections are assigned to one sub-image.

As mentioned above, the image sections are preferably extracted by determining a mask which is applied to the images of the process sequence in order to extract the image sections. The parts of the mask which result in the extraction of the image sections are referred to as elements of the mask. The mask can be determined on the basis of the above-mentioned tessellation of (a region of) the images of the process sequence. The elements which result from the tessellation and correspond to the image sections are the elements of the mask.

Preferably, not all but only a part of the image content of the images of the process sequence is respectively used for tracking. This part is preferably described by one or more regions of the image. Such a region can be masked by the aforementioned mask in order to extract the image sections. If there are several regions, this can also of course be performed in the same manner for the other regions. Thus, a mask is preferably determined for a region or for each region which corresponds in size to the respective region. Only sections within said region are then extracted by applying the mask. In accordance with the invention, the masked regions are preferably tracked. In other words, the set of image sections extracted from the regions by masking are used for tracking. In accordance with a preferred embodiment, the mask is fixed relative to each region throughout the sequence of process images, while as explained in more detail in EP 08 169 422.6 which corresponds to U.S. Ser. No. 12/621,881, the change in the position of the region from image to image within the process sequence and thus the change in the position of the set of image sections is tracked. Thus, the entire region is not tracked, as described in EP 08 164 422.6, but rather only the masked region. Since at least the majority of the image content of the masked region preferably undergoes similar changes in position, the reliability of tracking based on the masked region is increased as compared to tracking based on an unmasked region.

As mentioned above, the sub-images can be grouped according to their similarity, such that sub-images which undergo similar changes in position are placed in the same group. Therefore, a respective mask can be determined on the basis of the sub-images of one of the respective groups, in particular on the basis of the positions of the sub-images of said group. Different masks are preferably determined or in other words established for different groups in this way. Preferably, each group represents a different change in position, in particular different trajectories. Therefore, each group in particular exhibits a different correlation between the sub-images of the group and the changes in the position of the treatment body part. Thus, in accordance with one embodiment, the same region is masked by different masks and the resulting different masked regions can all be tracked. The tracked different masked regions will undergo different changes in position which correlate differently with the position and/or changes in the position of the treatment body part. Nevertheless, the changes in the position of the treatment body part as predicted on the basis of the different masked regions will ideally be the same. Reliability can thus be increased by using different masks. If the predicted positions and/or changes in the position of the treatment body part are not the same, an average (for example, a weighted average) of the different predicted positions and/or changes in position can be calculated. In particular, this average is used to control the guidance of the treatment beam. In particular, the positions and/or changes in position which are based on a larger part of the process image and/or which exhibit a greater correlation with the movement of the treatment body part can be weighted more strongly.

In other words, a region is masked in one of the images of the process sequence, for example in accordance with EP 08 169 422.6 and the corresponding U.S. Ser. No. 12/621,881. A region masked by the same mask is then sought in another image of the process sequence, in particular the next image. The region has the same geometry, and its image content as let through by the mask exhibits the greatest similarity to the image content of the masked region of the previous image. The determined position of the masked region in the latter image differs in particular from the position of the masked region in the previous image. Thus, there is a change in the position of the masked region from image to image within the process sequence. This change in position is preferably tracked and in particular describes a trajectory of an indicator body part, the movement of which correlates (in particular in a known manner) with the treatment body part.

The term "different masked regions" covers both different regions masked by different masks and the same region masked by different masks.

As mentioned above, the sub-images of an image of the advance sequence can be determined by sub-dividing (for instance tessellating) the image of the advance sequence (or a region of it) into sub-images, in particular according to a predetermined sub-division pattern (for example, a predetermined tessellation). In accordance with another embodiment, a predetermined sub-division pattern is not used, and the sub-images are rather generated, in particular flexibly and dynamically, during a process of determining the sub-images. Thus, the sub-division pattern which results from this process of determining the sub-images can differ for different advance sequences such as are in particular acquired from different patients. The process for determining the sub-images, in particular the location and/or size and/or shape of the sub-images, is in particular a process which identifies contiguous parts of the images which undergo similar changes in position in the advance sequence. This can be achieved by sub-dividing the image into a plurality of micro-images and performing on each micro-image the same process as described above for the sub-image and then combining contiguous micro-images which undergo similar changes in position, to form a sub-image. Preferably, a process is used which can be described as a dynamic growth process of the contiguous parts. A micro-image is then a kind of seed for this growth process. This can in particular be achieved in the following way. A micro-image is selected from an image of the advance sequence. The changes in the position of this micro-image are determined (from image to image within the advance sequence). Another micro-image which is contiguous with (adjacent to) the first micro-image is selected from the image of the advance sequence and checked as to whether it undergoes similar changes in position. As mentioned above, "similar changes in position" are changes in position which are similar to the changes in the position of at least one of the previously selected micro-images or similar to the same predetermined changes in position, i.e. the same as the predetermined changes in position which the changes in the position of the previously selected micro-image are similar to. The term "similar changes in position" also generally covers the term "identical changes in position". Thus, changes in position are also referred to as being similar when they are not just similar but identical.

The aforementioned step is preferably repeated for more and more micro-images which are contiguous with the preceding micro-images. In each such step, a micro-image is only added to a set of contiguous micro-images if it undergoes similar changes in position. This process is for instance continued for a predetermined number of steps or until there are no more contiguous micro-images which undergo similar changes in position. This results in a final set of micro-images which are contiguous and which undergo similar changes in position. This final set of micro-images is determined to be a sub-image. Preferably, a set of sub-images is thus determined, on the basis of which a set of image sections is extracted. Thus, in order to determine another sub-image, a new micro-image is selected which is not part of any of the previously determined sub-images, and the process of substituting (adding) other contiguous micro-images is repeated.

As stated above, a correlation between the changes in the position of indicator body parts and changes in the position of the treatment body part is preferably known. Corresponding correlation data are preferably provided which in particular describe the correlation between the trajectory of the indicator body part and the trajectory of the treatment body part. EP 08 169 422.6 and EP 09 160 153.4 describe how the correlation data can be generated. As for instance described in EP 09 160 153.4, three-dimensional CT data acquired before the treatment body part is treated can be used to determine the correlation between the trajectory of the indicator body part and the trajectory of the treatment body part. The advantage of this, as described in EP 09 160 153.4, is that the treatment body part can be more easily identified in the three-dimensional CT images than in two-dimensional x-ray images. The correlation information obtained is then transferred to two-dimensional space, in order to use the correlation for the images of the process sequence which are preferably only two-dimensional.

As mentioned above, the representation of the indicator body parts is preferably tracked by the method described above. A position of the treatment body part is determined on the basis of this tracking, i.e. on the basis of the determined changes in the position of the representation of the indicator body parts (in the extracted image sections) and on the basis of the correlation data.

Preferably, imaging geometry data are additionally provided which describe the position of the imaging geometry relative to the treatment beam, in particular relative to a default path of the treatment beam and/or relative to a region within which the treatment beam can be guided by a control device of a treatment beam system. Thus, the imaging geometry data allow the position of a beam to be calculated relative to the images. Alternatively or additionally, the correlation data allow the position of the treatment body part in the images of the process sequence (or relative to the images of the process sequence) to be calculated two-dimensionally. In particular, two analytical devices are provided which generate images of the body from different directions. The position of the treatment body part is then in particular determined on the basis of the correlation data in different images generated from different directions. Since the imaging geometry for all analytical devices is known from the imaging geometry data, the position of the treatment body part can be calculated three-dimensionally from the two respective positions of the treatment body part in the two images generated from different directions. It is thus possible in accordance with the invention to calculate the position of the treatment body part two-dimensionally (with respect to the two-dimensional images) or three-dimensionally.

If the position of the treatment body part is known, then a path for the treatment beam can be calculated on the basis of the imaging geometry data, such that the treatment beam passes through the treatment body part. If the diameter of the treatment beam is smaller than the treatment body part, the treatment body part can of course be scanned by the treatment beam in accordance with predefined scanning patterns. In particular, control data are determined on the basis of the determined position of the treatment body part and on the basis of the imaging geometry data and are used to control a treatment device which emits the treatment beam in such a way that the emitted treatment beam hits the treatment body part.

The method in accordance with the invention is in particular a data processing method. The data processing method is preferably performed using technical means, in particular a computer. The computer in particular comprises a processor and a memory in order to process the data, in particular electronically. The calculating steps described are in particular performed by a computer. Steps of determining or calculating are in particular steps of determining data within the framework of the technical data processing method, in particular within the framework of a program. A computer is in particular any kind of data processing device. A computer can be a device which is generally thought of as such, for example desktop PCs or notebooks or netbooks, etc., but can also be any programmable apparatus, such as a mobile phone or an embedded processor. In particular, a computer can comprise a system (network) of "sub-computers", wherein each sub-computer represents a computer in its own right. A computer in particular comprises interfaces in order to receive data and/or to perform an analog-to-digital conversion.

Where data are "provided", this means that they are ready for use by the method or program in accordance with the invention. The data can achieve this state of being "ready for use" by for example being generated, in particular detected or captured (for example by analysis apparatuses) or by being input (for example via interfaces). The data can also achieve the state of being provided by being stored in a data storage (for example a ROM, RAM, CD and/or hard drive) and thus ready for use within the framework of the method or program in accordance with the invention. The expression "providing data" emcompasses (within the framework of a data processing method) in particular that the data are determined by the data processing method or program. The meaning of "providing data" in particular encompasses also that the data are received by the data processing method or program, in particular to further process the data by the data processing method or program. Thus "providing data" can mean for instance to wait for a reception of data and to receive the data. The received data can be for instance inputted by the interface. "Providing data" can also mean that the data processing method or program performs steps to (actively) acquire the data from a data source, for instance a data storage (for instance ROM, RAM, data base, hard disk etc.) or via the interface (for instance from another computer or a network).

The methods described herein are in particular implemented as a program (computer program). In particular, all the steps of one of the aforementioned methods are implemented by a program. The program causes a computer to perform one of the methods described herein, in particular when running on a computer and/or when loaded on a computer.

The present invention is also directed to a program storage medium on which the aforementioned program is stored.

Within the framework of the invention, computer programs can be embodied by hardware and/or software (this also includes firmware, resident software, micro-code, etc.). Within the framework of the invention, computer programs can take the form of a computer program product which can be embodied by a computer-usable or computer-readable storage medium comprising computer-usable or computer-readable program instructions, "code" or a "computer program" embodied in said medium for use on or in connection with the instruction-executing system. Such a system can be a computer; a computer can be a data processing device comprising means for executing the computer program elements and/or the program in accordance with the invention. Within the framework of this invention, a computer-usable or computer-readable medium can be any medium which can include, store, communicate, propagate or transport the program for use on or in connection with the instruction-executing system, apparatus or device. The computer-usable or computer-readable medium can for example be, but is not limited to, an electronic, magnetic, optical, electromagnetic, infrared or semiconductor system, apparatus or device or a medium of propagation such as for example the Internet. The computer-usable or computer-readable medium could even for example be paper or another suitable medium onto which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

The present invention is also directed to a method of controlling a treatment beam. The method in particular includes the step of generating the advance image data and the process image data by analysing the body by using in particular at least one analytical device. The data are generated in particular based on images generated by the analytical devices. The generated data are in particular stored in a data storage of the computer. The stored data are in particular sent to the program or data processing method to be received by the program or data processing method. Furthermore, the method in particular includes a step of controlling the position of the treatment beam (of a treatment beam system) on the basis of the position of the treatment body part which position was determined by the method described herein. Thus, the position of the treatment beam is in particular controlled in dependence on data describing the position (for instance average position) of the treatment body part so that the treatment beam passes through the treatment body part. For controlling the position of the treatment beam in particular a control device for controlling the position of the treatment beam is used.

The present invention is also directed to a computer on which the aforementioned program is running or into the memory of which the aforementioned program is loaded. The present invention is in particular directed to any system which includes such a computer, in particular the treatment beam system mentioned above.

The present invention is also directed to a signal wave, in particular a digital signal wave, which carries information which represents the aforementioned program.

The aforementioned program in particular comprises code which is adapted to perform the steps of any one of the methods described herein, in particular all the respective steps of the respective methods.

The present invention is also directed to a treatment beam system which in particular comprises a treatment device which is adapted to emit the treatment beam (ionising radiation) being used. The treatment beam system also includes the aforementioned computer on which the aforementioned program is running or into the memory of which the aforementioned program is loaded. The treatment beam system preferably also comprises at least one analytical device for analysing the body and generating the advance image data and the process image data. Preferably, (at least) two analytical devices are provided which analyse the body from different directions, for example using x-rays. The treatment device preferably includes a control device for controlling the position of the treatment beam. In particular, the position of the treatment beam is controlled in accordance with the position of the treatment body part which is determined in accordance with the method described herein, in particular by means of the computer on which a corresponding program is running.

The position of the treatment body part can be determined on the basis of just one group of image sections which are extracted from an image of the process sequence and then tracked. The changes in the position of the group of image sections from image to image within the process sequence describe a trajectory. The trajectory is for instance determined by using the trajectory of the aforementioned masked region or by determining an average of all the trajectories of the image sections of the group. As mentioned above, it is however also possible to determine different (average) trajectories for different groups of image sections. Correlation data are then preferably provided which describe the correlation between the different (average) trajectories and the trajectory of the treatment body part. These correlation data are used to determine the trajectory of the treatment body part on the basis of different trajectories of groups of image sections. Preferably, the trajectory of the treatment body part is calculated for each group of the image section, on the basis of the correlation data. The calculated trajectories of the treatment body part ideally coincide with each other. It is of course also possible for the calculated trajectories to differ from each other, in which case an average trajectory can for example be calculated. When calculating the average, it is of course also possible for some of the different trajectories of the indicator body parts to be weighted more strongly than others, in particular those which are based on a larger part of the images of the process sequence and/or for which the corresponding correlation data exhibit a greater correlation with the trajectory of the treatment body part than others.

Additional features and advantages of the present invention are disclosed in the following detailed description of embodiments of the invention.

Figure 1:
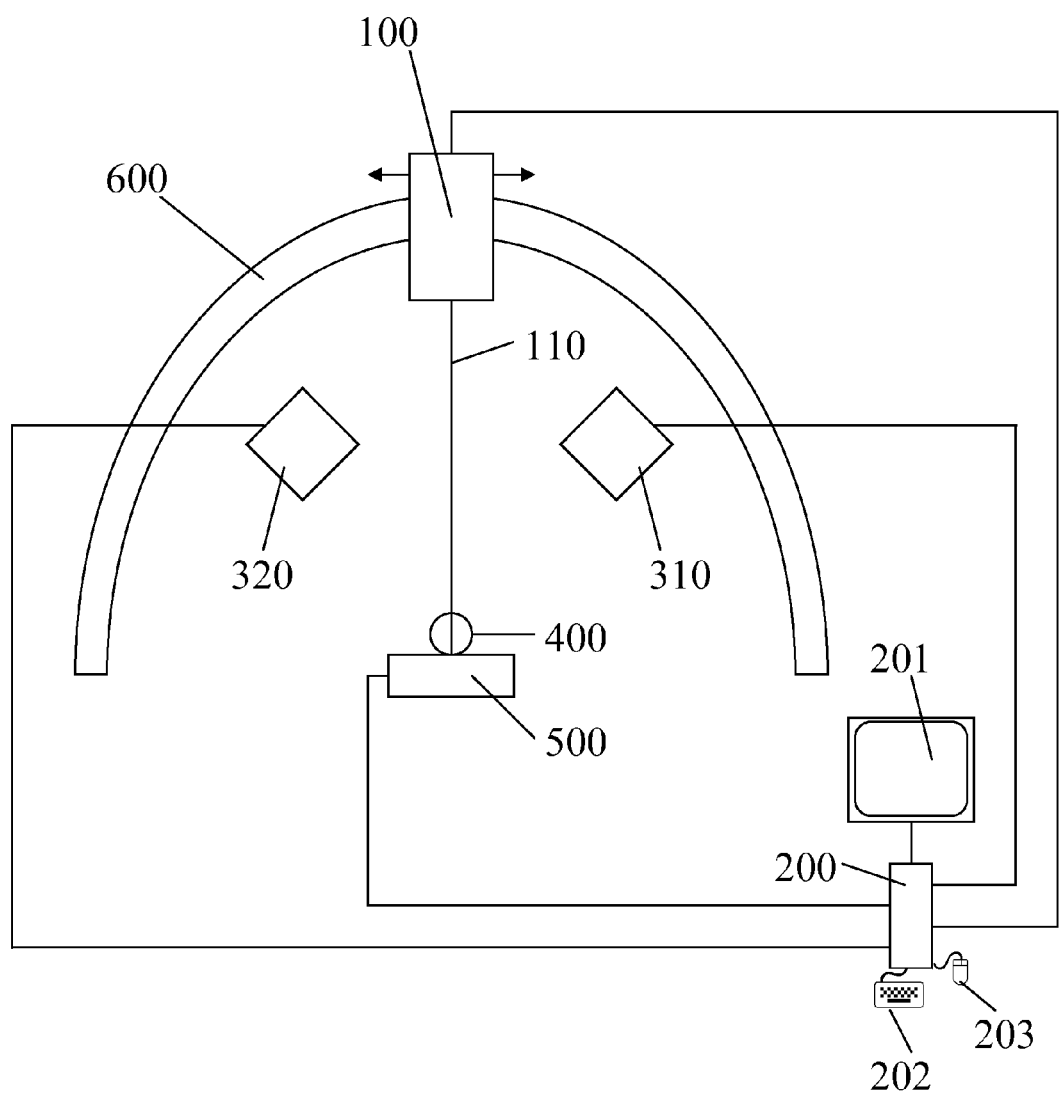
FIG. 1 shows a treatment beam system.

FIG. 1 shows a treatment beam system in accordance with the invention. A treatment device 100 emits a treatment beam 110. The treatment device 100 can be moved as indicated by the arrows, thus guiding the treatment beam 110. A computer 200 is electrically connected to the treatment device 100 in order to control the guidance of the treatment beam 110 by means of control signals. A screen 201, a keyboard 202 and a mouse 203 are connected to the computer 200. The computer 200 also controls analytical devices 310 and 320. The analytical devices 310 and 320 are in particular x-ray devices which take x-ray images of a patient 400. The computer 200 is connected to the analytical devices 310 and 320 in order to receive advance image data (before the treatment) and process image data (during the treatment) from the analytical devices 310 and 320. In particular, the computer 200 is also configured to control the image acquisition performed by the analytical devices 310 and 320. There is preferably an electrical connection between the analytical devices 310 and 320 and the computer 200 in order for the computer 200 to send control signals to the analytical devices 310 and 320 and/or receive the aforementioned data from the analytical devices 310 and 320. The patient 400 is lying on a table 500. The analytical devices 310 and 320 and the treatment device 100 are supported by a support structure 600. In order to control the relative position between the treatment beam 110 and the patient 400, it is also possible to move the table 500 so as to reposition the patient 400 relative to the treatment beam 110. In short, the treatment beam system is preferably configured to control the position of the treatment beam 110, in particular relative to the patient 400. This is in particular performed by the computer 200. Additional, assisting control devices can for instance be integrated into the treatment device 100 and/or the table 500 and preferably co-operate with the computer 200.

The method described above is preferably used to correctly control the position of the treatment beam 110 relative to the patient 400. A program which represents an implementation of said method is preferably stored and/or running on the computer 200. Said program tracks the indicator body parts on the basis of the advance image data and the process image data. The computer 200 preferably calculates the position of the treatment body part on the basis of the aforementioned known correlation between the position of the indicator body part and the position of the treatment body part. The computer preferably also has information on the imaging geometry of the analytical devices 310 and 320 relative to the location of the treatment beam 110. The computer is thus able to calculate the location of the treatment beam 110 relative to the treatment body part on the basis of the aforementioned data. By comparing the calculated positions, the position of the treatment beam 110 can be controlled so as to hit the treatment body part.

Figure 2:
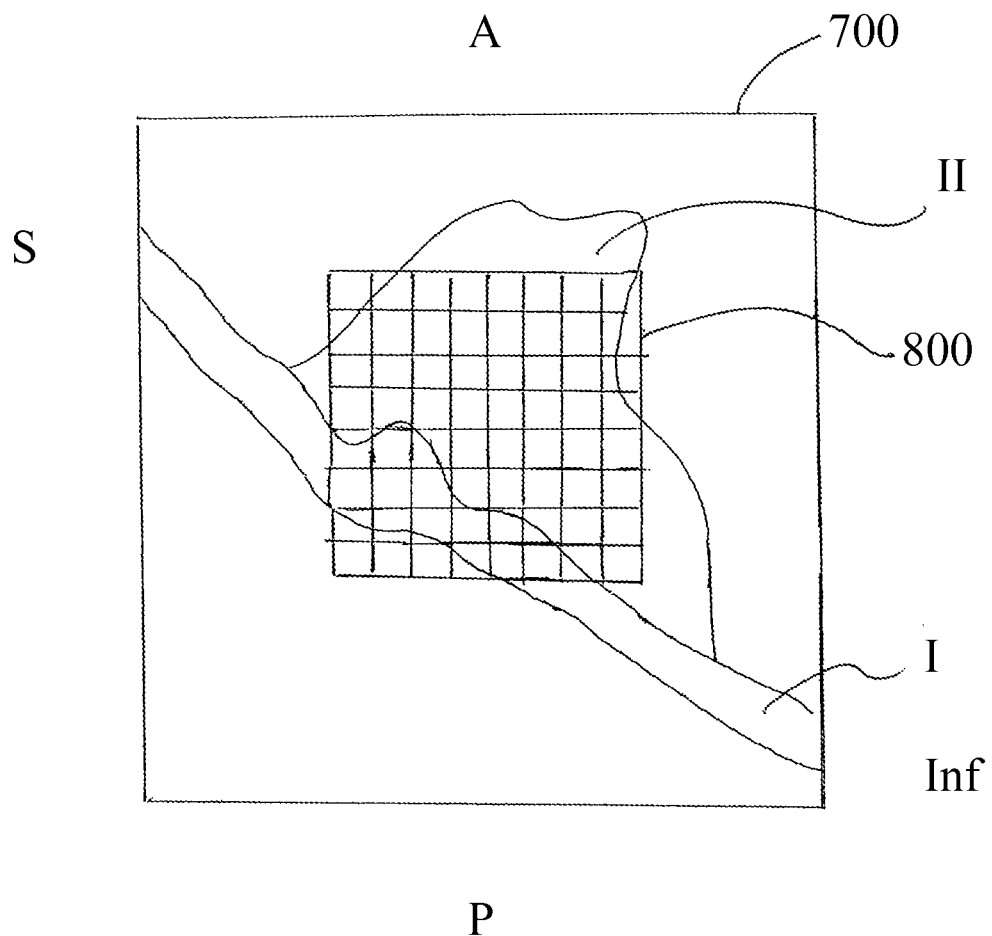
FIG. 2 shows an image of the advance sequence, including a tessellated region.

FIG. 2 shows an image of the advance sequence of images. The frame of the image is indicated by the reference sign 700. The frame of a region bears the reference sign 800. The region 800 is tessellated into a plurality of quadratic elements within the region 800. In the given example, there are 64 such elements within the region 800. The image comprises two image parts I and II. For example, the image part I shows a representation of indicator body parts which move in a first direction (the anterior-posterior direction), for instance a part of the chest, and the image part II shows indicator body parts which move in a different direction (the superior-inferior direction). An example of the indicator body parts in the image part II would be soft tissue which moves due to the breathing movement caused by the diaphragm.

The letter "A" indicates the anterior direction and the letter "P" indicates the posterior direction. The first part I of the image is assumed to move in the anterior-posterior direction due to the movement of the chest. The letter "S" indicates the superior direction and the letters "Inf" indicate the inferior direction. As mentioned above, it is assumed that the indicator body parts shown in the image part II move in the inferior-superior direction. The aforementioned movements of the indicator body parts shown in the images of the advance sequence are movements relative to the frames 700 of the images of the advance sequence of images.

The elements in the region 800 represent sub-images which are candidates for sub-images which undergo similar changes in position. Corresponding sub-images are preferably sought in a subsequent image of the advance sequence of images, wherein said corresponding sub-images can have a different position as compared to the previous image of the advance sequence. In other words, the sub-images can undergo changes in position relative to the frame 700 of the image of the advance sequence. The changes in the position of the sub-images are indicated for some of the sub-images in FIG. 3, which shows a co-ordinate system comprising an x-axis and a y-axis. The y-axis corresponds to the anterior-posterior direction shown in FIG. 2, and the x-axis corresponds to the left-right direction in the image shown in FIG. 2. The changes in the position of some of the sub-images are marked as crosses. The changes in position can for instance be calculated by calculating the difference between a position of a sub-image in the subsequent image of the advance sequence and the position of the corresponding sub-image in the previous image of the advance sequence. As mentioned above, "corresponding" means in particular that the image content is the same.

Figure 3:
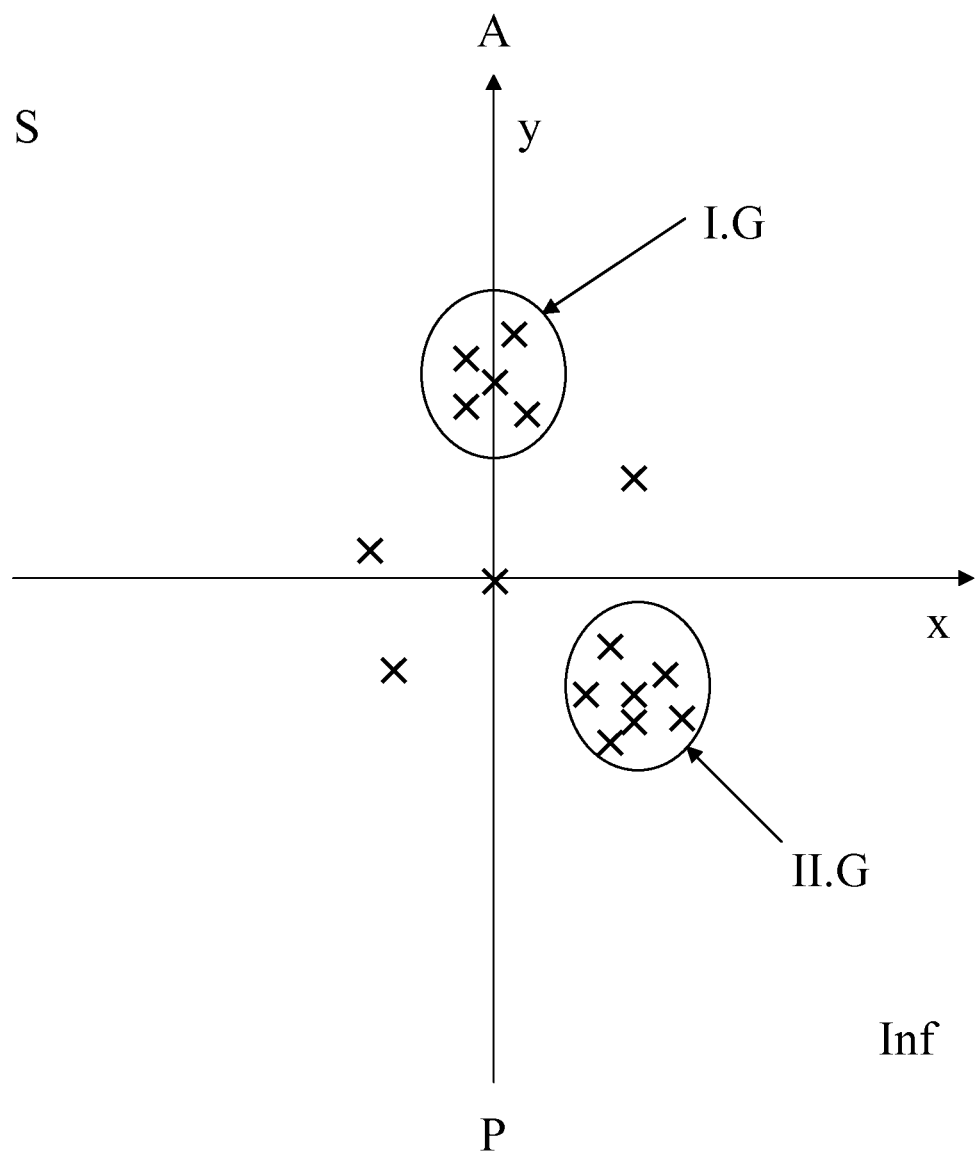
FIG. 3 shows a distribution of changes in the position of elements of the region shown in FIG. 2.

As can be seen from FIG. 3, a plurality of sub-images undergo changes in position in the y-direction. Another plurality of sub-images undergo changes in position in the inferior direction which is indicated as "Inf". There are accumulations of sub-images, which have been respectively circled in FIG. 3. The first one is indicated as "I.G", meaning "the first group". The other accumulation of sub-images is indicated as "II.G", meaning "the second group". Since the sub-images of the first group are close to each other, they are determined to be sub-images which undergo similar changes in position. The same applies to the sub-images of the second group. Alternatively, the members of the first group can for example be determined to be close to a predetermined change in position which is for instance a change in position represented by a change in the anterior direction (the y-direction) by a certain amount and which for instance corresponds to the centre of the first group as shown in FIG. 3.

Figure 4:
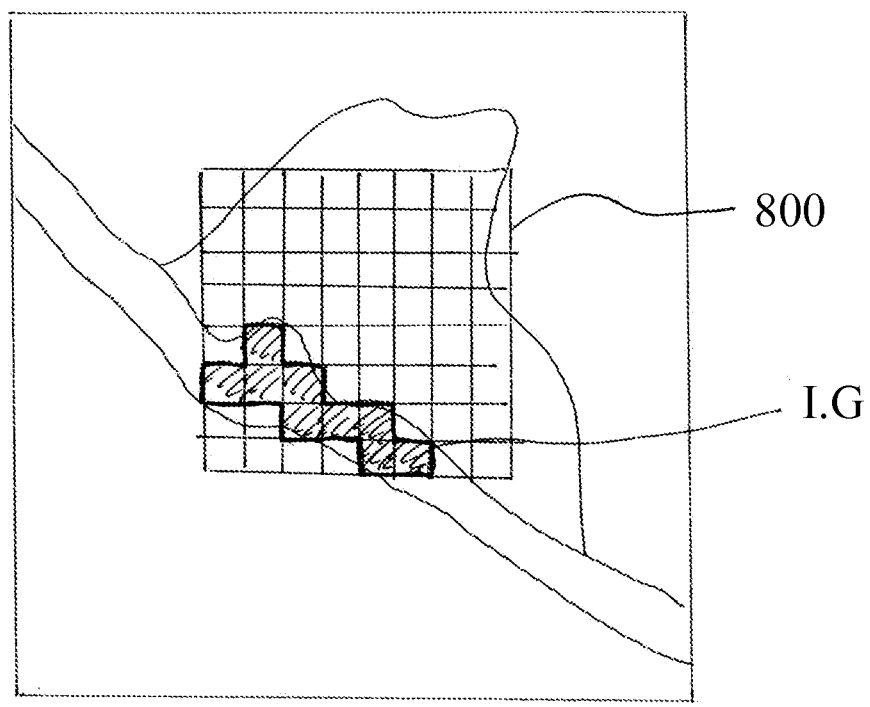
FIG. 4 shows a first group of elements of the region identified on the basis of FIG. 3.

The position of the first group of sub-images within the frame 800 of the region is shown in FIG. 4. The sub-images of the first group are shown as hatched squares. The sub-images have a particular relative position or distribution within the region and relative to the frame 800 of the region. This relative positional distribution is assumed to be fixed. As can be seen, the sub-images of a first group lie within the first part of the image and show indicator body parts (the chest) which move in the anterior-posterior direction.

Figure 5:
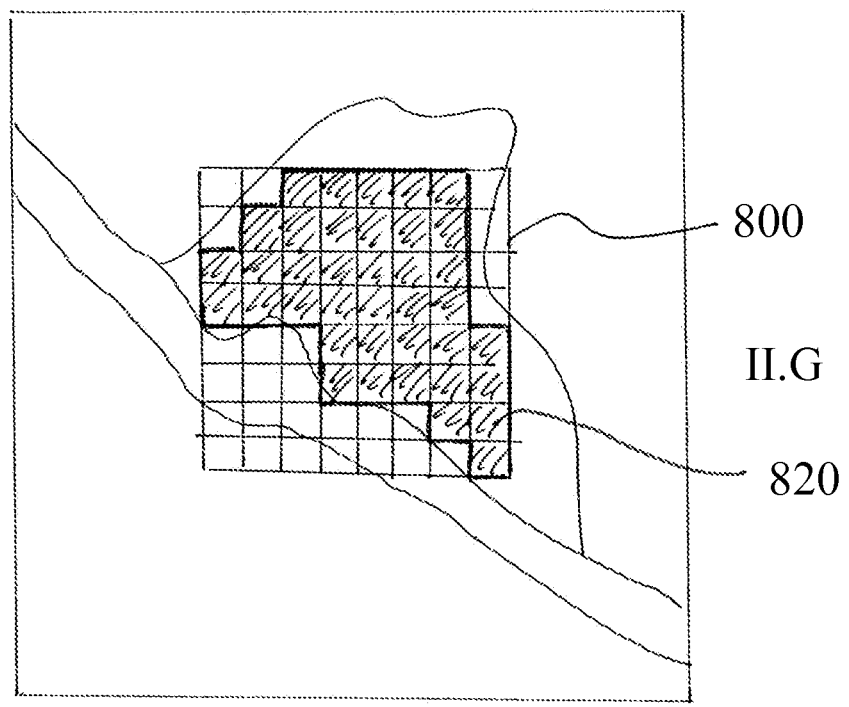
FIG. 5 shows a second group of elements of the region identified on the basis of FIG. 3.

FIG. 5 shows the sub-images of the second group within the region, again as hatched squares. These sub-images also have a fixed position relative to the frame 800 of the region. In particular, the sub-images have a relative positional distribution which is preferably fixed. In the given example, the sub-images are all contiguous with each other. However, this is not obligatory. It is also possible for individual sub-images of the same group to not be contiguous with any other sub-image of the same group.

As mentioned above, the relative positional relationship between the sub-images is preferably fixed and used to extract image sections within the process sequence. Specifically, a mask is applied to images of the process sequence which only lets through image sections which have a relative positional relationship as shown in FIG. 4 for the first group and in FIG. 5 for the second group.

Figure 6A:
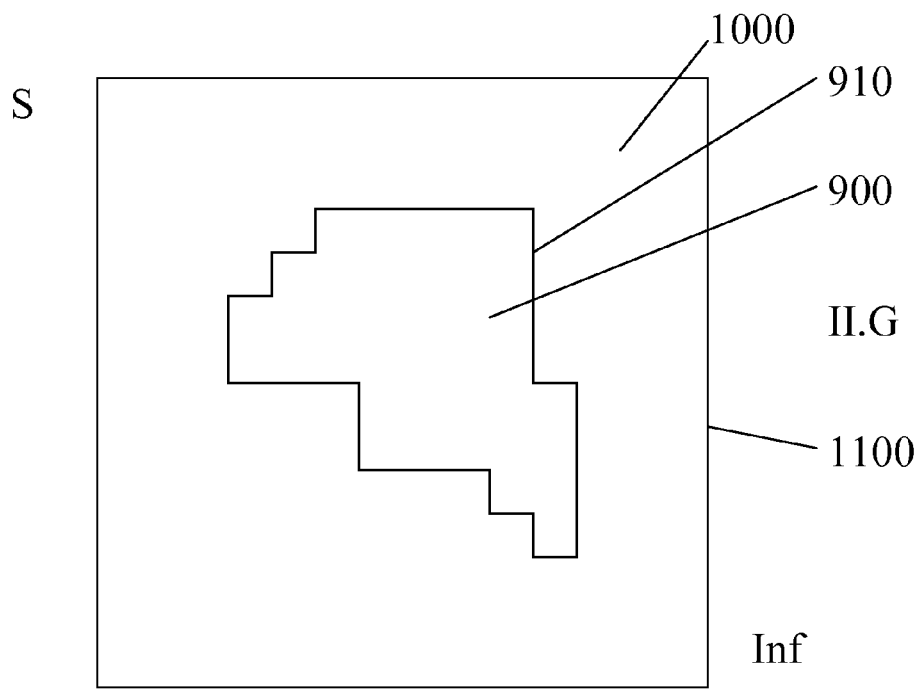
FIG. 6a shows a set of extracted image sections in an image of the process sequence.
Figure 6B:
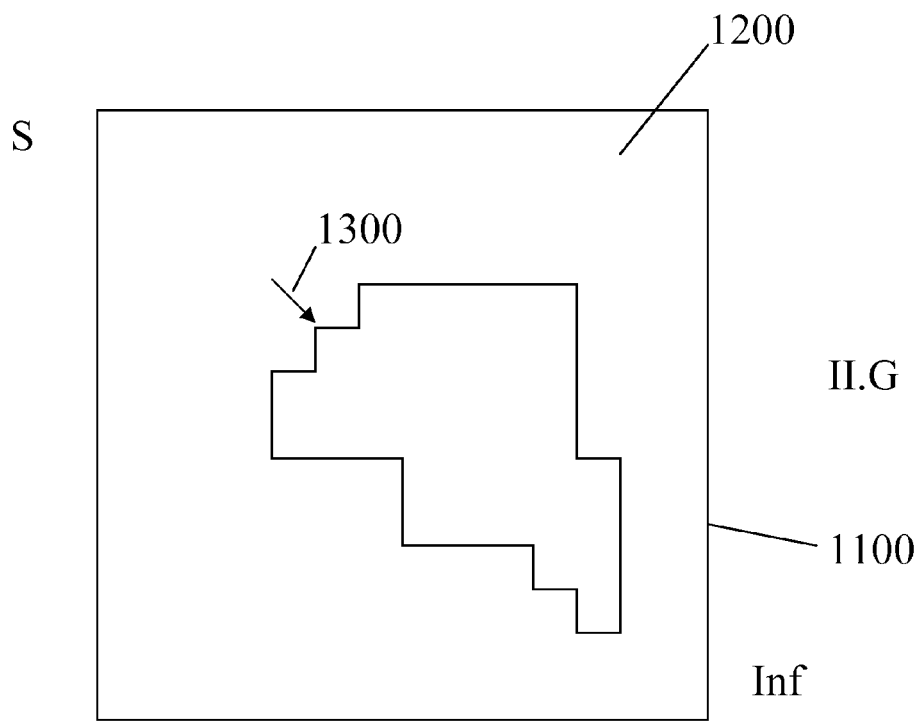
FIG. 6b shows a subsequent image of the process sequence in which the set of image sections from 6a has been tracked.

The examples shown in FIGS. 6a and 6b relate to the extraction of image sections which correspond to the second group shown in FIG. 5. A mask 900 is thus applied which only lets through image sections within the contour 910 of the mask 900 for tracking purposes. The mask 900 can be moved relative to the frame 1100 of the image 1000 of the process sequence. The image sections extracted by applying the mask 900 to the image 1000 are analysed as to whether they correspond to the image content of the sub-images 820 shown in FIG. 5, i.e. to the image content of the sub-images of the second group. If the image content extracted from the image 1000 by applying the mask 900 is determined to correspond to the image content of the sub-images 820 for a particular position of the mask 900 relative to the frame 1100, then the image sections thus extracted are deemed to be a group of image sections which undergo similar changes in position.

The same mask 900 is preferably applied in a subsequent image 1200 of the process sequence, in order to find a group of image sections for which the image content corresponds to the group of image sections found in the previous image 1000 of the process sequence, such as that shown in FIG. 6a. As can be seen, the group of image sections has undergone a change in position, as indicated by an arrow 1300. The vector 1300 corresponds to the change in the position of the group of image sections. In other words, the vector 1300 corresponds to the change in the position of the mask 900 relative to the frame 1100 between FIG. 6a and FIG. 6b.

In other words, the vector 1300 represents the change in the position of the group of image sections which show indicator body parts which undergo similar changes in position. Thus, the indicator body parts shown within the contour 910 in FIG. 6a are tracked in FIG. 6b and have moved by a vector 1300 between FIG. 6a and FIG. 6b.

It is then possible to calculate the position of the treatment body part and/or the change in the position of the treatment body part on the basis of a known correlation between the movement of the indicator body parts (as described by the vector 1300) and the movement of the treatment body part and preferably on the basis of the known relative position between the indicator body parts and the treatment body part. As already described above, it is then possible to control the position of the treatment beam 110 on the basis of this determination of the change in position, such that the treatment beam 110 hits the treatment body part even when the treatment body part undergo vital movements.

The invention claimed is:

1. A method in the field of medicine for tracking image sections which represent indicator body parts of a body in a process sequence of images in order to determine the position of another body part referred to as a treatment body part, wherein changes in the position of the indicator body parts are used as an indicator for changes in the position of the treatment body part of the body which is to be treated using a radiation treatment beam, said method comprising the following steps performed by a computer:
    providing advance image data generated before the treatment, the advance image data describing an advance sequence of a plurality of images representing a result of an advance analysis of the body;
    providing process image data which describe the process sequence of images, wherein the process sequence of images represents a result of a process analysis of the body which is performed after the advance analysis and during the treatment;
    providing correlation data which describe the correlation between a cyclic trajectory of the indicator body part and a trajectory of the treatment body part;
    determining by means of a computer, on the basis of the advance image data, a set of a plurality of sub-images in the respective images of the advance sequence, the plurality of sub-images undergoing similar changes in position in the advance sequence and undergoing a cyclic trajectory in the advance sequence;
    extracting by means of the computer during treatment, on the basis of the process image data and the determined set of sub-images, a set of image sections from the images of the process sequence which undergo similar changes in position and which have an image content which corresponds to the image content of the determined sub-images;
    tracking the set of extracted image sections in the process sequence as a group by means of a computer; and,
    determining a position of a treatment body part during the treatment on the basis of the position of the tracked representation of the indicator body parts and on the basis of the correlation data by means of the computer.

2. The method according to claim 1, further comprising the steps of:
    providing similarity conditions which describe conditions for whether the sub-images undergo similar changes in position, wherein the similarity conditions are conditions for whether the changes in the position of sub-images are similar to each other or not and/or conditions for whether the changes in the position of sub-images are similar to predetermined changes in position or not; and,
    determining the sub-images which undergo similar changes in position by comparing the changes in the position of the sub-images with the similarity conditions.

3. The method according to claim 2, wherein the predetermined changes in position defined by the similarity conditions are determined on the basis of patient positioning data and/or advance vital data,
    wherein the patient positioning data describe the position of the patient relative to the imaging geometry used for acquiring the advance sequence of images, and the advance vital data describe a vital parameter of the body at the time the respective images of the advance sequence are acquired; and/or
    comprising the steps of:
    determining the relative positional relationship of the sub-images; and,
    constraining the search for image sections in subsequent images, such that their relative positional relationship is at least similar to the relative positional relationship determined for the sub-images, for tracking the extracted image sections in the process sequence.

4. The method according to claim 2, comprising the steps of:

identifying different groups of sub-images, wherein each group respectively fulfils one of a number of different similarity conditions;

extracting groups of image sections which respectively correspond to the groups of sub-images; and, tracking each group of extracted image sections separately in the process sequence.

5. The method according to claim 1, comprising the steps of:
  a) determining a mask comprising elements which exhibit a relative positional relationship which represents the constraints and the size and shape of the elements corresponding to the size and shape of the image sections to be extracted, wherein the mask has the property of being able to be freely positioned relative to an image to which the mask is applied, and the property of letting through, for further processing by the method only, the part of the image which is covered by the elements;
  b) applying the mask to an image of the process sequence for a plurality of different positions relative to the image, in order to generate a plurality of sets of image sections which have been let through by the mask;
  c) analysing the plurality of sets of image sections which have been let through by the mask as to whether their image content is similar to the image content of the determined sub-images or to a previously determined set of image sections;
  d) determining a set of image sections by selecting the set of image sections which is most similar; and,
  repeating Steps b) to d) in order to track the set of image sections in the process sequence.

6. The method according to claim 5, wherein:
  the elements of the mask have a position relative to each other which is such that they are included in a region which is smaller than the process image;
  the step of applying the mask to the process image includes the step of blocking the parts of the image which are not covered by the region from further processing, such that only image sections extracted from a region of the process image are tracked, wherein the position of the region can change from process sequence to process sequence due to displacement of the mask; and
  the method also comprises the step of determining the changes in the position of the region, in order to represent the changes in the position of the indicator body parts represented by the tracked image sections.

7. The method of claim 6, comprising the steps of:
  establishing different masks which correspond to different groups; and,
  separately tracking the representations of different indicator body parts in the process sequence by separately tracking different masked regions in the process sequence.

8. The method according to claim 1, comprising the steps of:
  providing advance vital data which describe a vital parameter of the body at the time the respective images of the advance sequence are acquired;
  determining a correlation between changes in the vital parameter and changes in the relative positional relationships of the sub-images;
  providing process vital data which describe a change in the vital parameter between a previous process image and the current process image;
  changing the constraint for the relative positional relationship in accordance with the determined correlation and the process vital data; and applying said constraint in order to track the extracted image sections in the current process image.

9. The method according to claim 1, comprising the steps of:
  determining a micro-image by selecting it from an image of the advance sequence;
  determining, step by step, additional micro-images which are contiguous with at least one previously determined micro-image and which undergo at least similar changes in position; and,
  determining the determined micro-images to be a sub-image if no more micro-images are determined.

10. The method according to claim 1, further comprising the step of determining mathematical expressions for describing the changes in the position of the sub-images, wherein the type of mathematical expression is in particular at least one of the following:
  a function of a value, wherein the value describes a magnitude of a change in the position of a sub-image in the advance sequence or an angle which describes a change in direction;
  a function of a vector which describes a change in the position of a sub-image in the advance sequence;
  a trajectory which describes a path of a sub-image in the advance sequence; and,
  a function of a time or frequency at which a sub-image undergoes a cyclic trajectory in the advance sequence.

11. The method according to claim 1 for determining the position of a treatment body part of the body to be treated using ionising radiation, wherein the process sequence is assumed to represent different trajectories of different indicator body parts which correlate differently with a trajectory of the treatment body part which is to be treated using radiation, said method comprising the steps of:
  providing correlation data which describe the respective correlation between the different trajectories of the different indicator body parts and the trajectory of the treatment body part;
  separately determining a position of the treatment body part for each of the separately tracked representations of the different indicator body parts, on the basis of the position of the separately tracked representation of the indicator body part and on the basis of the correlation data; and
  determining an average position of the treatment body part on the basis of the separately determined positions.

12. A computer program embodied on a non-transitory computer readable medium which, when running on a computer or when loaded onto a computer, causes the computer to perform the method according to claim 1.

13. A method for controlling the position of a treatment beam which comprises the method of claim 1 and which further includes the following steps:
  generating the advance image data and the process image data by analysing the body by means of analytical devices; and,
  controlling the position of the treatment beam on the basis of the determined position of the treatment body part.

14. A treatment beam system, comprising:
  a treatment device which is designed to emit a treatment beam;
  a computer on which a program is running or into the memory of which the program is loaded, wherein the program, when running on the computer or when loaded onto the computer, causes the computer to perform the method according to claim 1 on the basis of the advance image data and the process image data; and, at least one analytical device for generating the advance image data and the process image data by analysing the body;

wherein the treatment beam system is configured to control a device for controlling the position of the treatment beam on the basis of the position of the treatment body part as determined by the computer.

* * * * *